US008932280B2

(12) United States Patent
Isaacson et al.

(10) Patent No.: US 8,932,280 B2
(45) Date of Patent: *Jan. 13, 2015

(54) METHODS, SYSTEMS AND DEVICES FOR PERFORMING ELECTROSURGICAL PROCEDURES

(75) Inventors: James D. Isaacson, Salt Lake City, UT (US); Paul R. Borgmeier, Salt Lake City, UT (US); Tremayne Paul Mikalauski, Draper, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 1052 days.

This patent is subject to a terminal disclaimer.

(21) Appl. No.: 12/957,177

(22) Filed: Nov. 30, 2010

(65) Prior Publication Data

US 2011/0125152 A1      May 26, 2011

Related U.S. Application Data

(63) Continuation of application No. 11/552,873, filed on Oct. 25, 2006, now Pat. No. 7,842,033, which is a continuation of application No. 10/412,698, filed on Apr. 4, 2003, now Pat. No. 7,128,741.

(51) Int. Cl.
| | |
|---|---|
| *A61B 18/10* | (2006.01) |
| *A61B 18/12* | (2006.01) |
| *A61B 18/14* | (2006.01) |
| *A61B 17/00* | (2006.01) |

(52) U.S. Cl.
CPC ... *A61B 18/1402* (2013.01); *A61B 2017/00221* (2013.01)
USPC .............................................. 606/32; 606/41

(58) Field of Classification Search
USPC .............................. 606/32–35, 37–41, 45–48
See application file for complete search history.

(56) References Cited

U.S. PATENT DOCUMENTS

| | | | |
|---|---|---|---|
| 3,845,771 A | 11/1974 | Vise | |
| 4,510,939 A * | 4/1985 | Brenman et al. | 600/384 |
| 4,765,343 A | 8/1988 | Brenman et al. | |
| 4,878,493 A | 11/1989 | Pasternak et al. | |
| 5,242,440 A | 9/1993 | Shippert | |

(Continued)

OTHER PUBLICATIONS

Office Action dated Jul. 28, 2004, 4 pages, U.S. Appl. No. 10/412,698.

(Continued)

*Primary Examiner* — Michael Peffley
(74) *Attorney, Agent, or Firm* — Workman Nydegger

(57) ABSTRACT

Systems, methods, and instruments associated with controlling the operating modes of an electrosurgical instrument using control signals delivered in a wireless manner from the electrosurgical instrument to an electrosurgical generator. The electrosurgical instrument transmits wireless control signals to the electrosurgical generator to initiate delivery of electrosurgical energy. The control signals are delivered to the electrosurgical generator without the need for a conductive cord extending between the electrosurgical generator and the electrosurgical instrument. The energy is delivered to the electrosurgical instrument, in response to the wireless control signals, along a path through an electrode and the physician utilizing the electrosurgical instrument and/or a conductive path external to the physician. The electrode upon which the physician rests provides a path for the electrosurgical energy and optionally prevents burning of the physician during an electrosurgical procedure.

20 Claims, 8 Drawing Sheets

(56) References Cited

U.S. PATENT DOCUMENTS

| | | |
|---|---|---|
| 5,792,138 A | 8/1998 | Shipp |
| 5,951,552 A | 9/1999 | Long et al. |
| 5,961,514 A | 10/1999 | Long et al. |
| 6,039,734 A | 3/2000 | Goble |
| 6,120,501 A | 9/2000 | Long et al. |
| 6,235,027 B1 | 5/2001 | Herzon |
| 6,423,059 B1 | 7/2002 | Hanson et al. |
| 6,454,764 B1 * | 9/2002 | Fleenor et al. ............ 606/32 |
| 6,551,312 B2 * | 4/2003 | Zhang et al. ............ 606/41 |
| 6,786,905 B2 | 9/2004 | Swanson et al. |
| 7,128,741 B1 | 10/2006 | Isaacson et al. |
| 7,842,033 B2 | 11/2010 | Isaacson et al. |
| 8,449,541 B2 * | 5/2013 | Schneider ............ 606/45 |

OTHER PUBLICATIONS

Office Action dated Jan. 3, 2005, 5 pages, U.S. Appl. No. 10/412,698.
Office Action dated Jun. 16, 2005, 5 pages, U.S. Appl. No. 10/412,698.
Notice of Allowance and Fees Due dated Jun. 29, 2006, 6 pages, U.S. Appl. No. 10/412,698.
Office Action dated May 13, 2010, 5 pages, U.S. Appl. No. 11/552,873.
Notice of Allowance and Fees Due dated Sep. 9, 2010, 6 pages, U.S. Appl. No. 11/552,873.

* cited by examiner

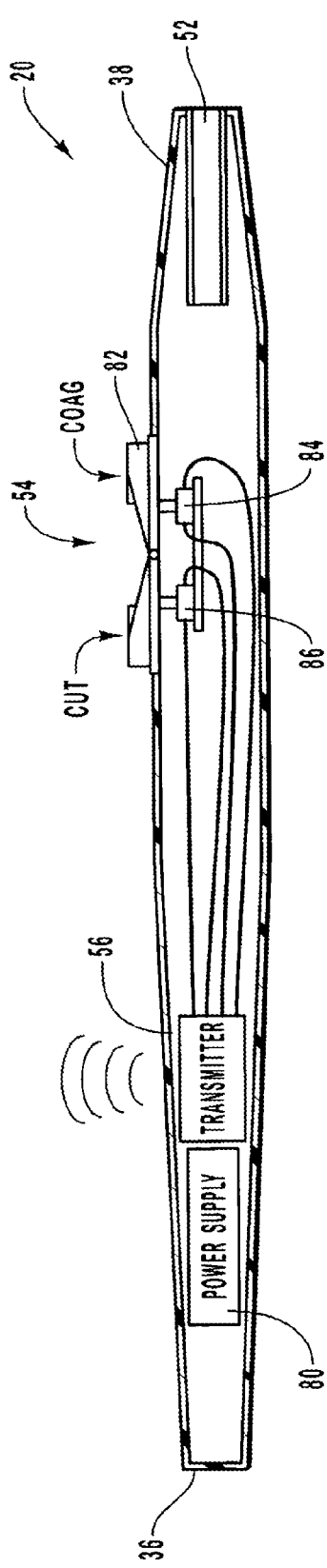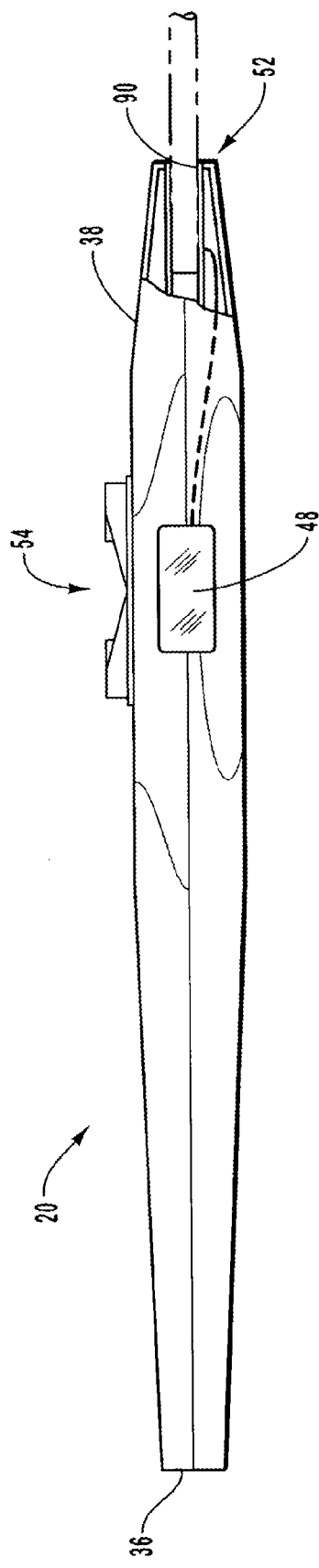
FIG. 4
FIG. 5

METHODS, SYSTEMS AND DEVICES FOR PERFORMING ELECTROSURGICAL PROCEDURES

CROSS-REFERENCE TO RELATED APPLICATIONS

This is a continuation application of U.S. patent application Ser. No. 11/552,873, filed Oct. 25, 2006, entitled "Methods, Systems, and Devices for Performing Electrosurgical Procedures", now U.S. Pat. No. 7,842,033, which is a continuation application of U.S. patent application Ser. No. 10/412,698, filed Apr. 4, 2003, entitled "Methods, Systems, and Devices for Performing Electrosurgical Procedures", now U.S. Pat. No. 7,128,741, the disclosure of each of which is incorporated herein by this reference in their entireties.

BACKGROUND OF THE INVENTION

1. The Field of the Invention

This invention relates to the field of electrosurgical instruments, systems, and methods. More particularly, the invention relates to electrosurgical systems, instruments, and methods that facilitate delivery of wireless signals to an electrosurgical generator to initiate delivery of electrosurgical energy to an electrosurgical instrument.

2. The Relevant Technology

As is known to those skilled in the art, modern surgical techniques typically employ radio frequency (RF) power to cut tissue and coagulate bleeding encountered in performing surgical procedures. For historical perspective and details of such techniques, reference is made to U.S. Pat. No. 4,936,842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical instrument for both cutting and coagulation. Every monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce a high current density in order to produce a surgical effect of cutting or coagulating tissue. The return electrode carries the same current provided to the electrode or tip of the electrosurgical instrument and back to the electrosurgical generator. Consequently, the return electrode must be large enough in effective surface area at the point of communication with the patient such that a low density current flows from the patient to the return electrode. In the event that a relatively high current density is produced at the return electrode, the temperature of the patient's skin and tissue will rise in this area and may result in an undesirable patient burn.

To make the electrical connection between the electrosurgical generator and the electrosurgical instrument a cord, having an electrically conductive core, extends from the electrosurgical generator to the electrosurgical instrument. The cord has certain flexibility and weight characteristics that limit the ability of the physician during a surgical procedure. For example, the cord has a defined length that limits the range of motion provided to the physician using the active electrode. Additionally, having an elongated cord in an operating environment to provide the physician with greater range of motion may also cause problems. For instance, the cord may become wrapped around medical equipment and/or may tangle or trip the physician or other medical personnel. Consequently, use of an elongated electrical cord may be dangerous to the physician and other medical personnel in the operating environment.

In addition to the above, the weight of the cord electrically linking the generator and the active electrode limits the physician's ability to continually hold and use the active electrode. The weight of the cord continually pulls the end of the electrosurgical instrument to which it is attached. During use, therefore, the physician may become fatigued during a surgical procedure that requires extensive and continual use of the electrosurgical instrument.

Additionally, the flexibility of the cord linking the generator and the active electrode limits the effectiveness of the electrosurgical instrument. Each cord has a conductive core with insulation surrounding the same. During manufacture of the cord, certain physical characteristics and properties become associated with the cord. For instance, the combination of core and insulation define an initial orientation of the cord. This initial orientation may be changed as a physician, clinician or operator manipulates the electrosurgical instrument and moves the cord. Although moved to a new position, the core and insulation have a "memory" of the initial orientation and attempt to return to the initial orientation upon the physician, clinician, or operator releasing the tension or force applied to the cord. The force applied by the core and insulation to return the cord to the initial orientation limits the movement of the physician, clinician, or operator. More specifically, the physician, clinician, or operator of the electrosurgical instrument must continually overcome the force applied by the cord to return the cord to the initial orientation. Resultantly, the physician, clinician, or operator may become fatigued and may loose range of motion of the electrosurgical instrument.

Further, the "memory" associated with the cord may move the electrosurgical instrument from within the sterile field upon resting the electrosurgical instrument upon a table or other surface within the sterile field. For instance, as the cord moves to return to the initial orientation, the force applied by the cord upon the electrosurgical instrument may result in the instrument being moved out of the sterile field. This results in a time delay in the procedure as replacement instruments are retrieved and positioned for use.

BRIEF SUMMARY OF THE INVENTION

Generally, the present invention relates to systems, methods, and instruments associated with controlling the operating modes of an electrosurgical instrument using control signals that are delivered in a wireless manner from the electrosurgical instrument to the electrosurgical generator. Through using wireless technology to deliver the control signals, the electrosurgical system may initiate delivery of electrosurgical energy without the need for a conductive cord or member acting as a physical control path between the electrosurgical generator and the electrosurgical instrument. Therefore, the methods, systems, and instruments of the present invention eliminate the need for a physical control path between the electrosurgical generator and the electrosurgical instrument and utilize a wireless control path. Consequently, illustrative methods, systems, and instruments alleviate the problems associated with corded electrosurgical instruments by allowing a physician to freely move an electrosurgical instrument without being constrained by the length and flexibility of the electrical cord extending from the instrument to the electrosurgical generator. Hence, the physician may perform electrosurgical procedures in a less strenuous manner and within a safer environment than is currently the case.

According to one aspect of one exemplary configuration of the present invention, the electrosurgical system includes an electrosurgical generator that creates electrosurgical energy deliverable to an electrosurgical instrument. The generator delivers electrosurgical energy to the instrument in response to wireless signals or control signals transmitted by the) instrument to the generator. In an alternate embodiment, the instrument transmits the signals to an adapter that acts as an intermediary between the generator and the instrument and controls delivery of electrosurgical energy based upon the wireless signals received from the instrument.

Electrosurgical energy delivered to the electrosurgical instrument may pass through the physician. Alternatively, the electrosurgical energy may flow through a path that is external to the physician. Still in another configuration, the electrosurgical energy may flow through the physician and a conductive path external to the physician.

To aid with delivery of electrosurgical energy to the electrosurgical instrument, the system may include an electrode upon which the physician stands or rests during use of the electrosurgical instrument. The electrode provides a path for the electrosurgical energy to flow into the physician or into the conductive path external to the physician. In some circumstances, the electrode is self-limiting to prevent physician burns during the electrosurgical procedure. Embodiments of the present invention may also include similar electrodes disposed between the patient and the generator, where the electrode acts as a return electrode that provides a path for electrosurgical energy to return to the electrosurgical generator.

Additional features and advantages of the invention will be set forth in the description which follows, and in part will be obvious from the description, or may be learned by the practice of the invention. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 4 is a schematic representation of a cross-sectional side view of the electrosurgical instrument of FIG. 2 in accordance with one aspect of the present invention;

FIG. 5 is a schematic representation of a partial cross-sectional side view of the electrosurgical instrument of FIG. 2 in accordance with one aspect of the present invention;

DETAILED DESCRIPTION OF THE PREFERRED EMBODIMENTS

The present invention relates to systems, methods, and instruments associated with electrosurgical technology and procedures. Illustrative systems, methods, and instruments use wireless technology to deliver control signals from an electrosurgical instrument to an electrosurgical generator. In this manner, electrosurgical systems may initiate delivery of electrosurgical energy without the need for a physical control path, i.e., conductive cord, between the electrosurgical generator and the electrosurgical instrument. Therefore, the methods, systems, and instruments of the present invention eliminate the need for a control line and, in some circumstances, electrical communication lines between the electrosurgical generator and the electrosurgical instrument. Consequently, the methods, systems, and instruments alleviate the problems associated with corded electrosurgical instruments and allow a physician to perform electrosurgical procedures in a less strenuous manner and within a safer environment than is currently the case.

According to another aspect of one exemplary configuration of the present invention, in response to receiving control signals, electrosurgical energy is delivered to the electrosurgical instrument through a physician electrode and the physician resting thereupon. This is in contrast to existing systems where the electrosurgical energy is delivered to the electrosurgical instrument along an electrical communication line, such as a conductive cord extending between the electrosurgical generator and the electrosurgical instrument. In other configurations, the electrosurgical energy may be delivered through the physician electrode and one or more electrical paths included in the clothing, footwear, and/or gloves of a physician. In still another configuration, the electrosurgical energy is delivered using a conductive cord, without a control line, which extends from the electrosurgical generator to the electrosurgical instrument. This is again different from existing systems where a cord extending between the electrosurgical generator and the electrosurgical instrument includes a conductor member acting as a path for electrosurgical energy and a separate control signal conductor.

To ease with the explanation of the different and optional components and elements of the present invention, discussion will be made of exemplary embodiments of electrosurgical systems using one or more of the features and functions of the present invention. Although reference is made to various exemplary embodiments and associated features and functions, one skilled in the art may identify various other embodiments of the present invention.

Figure 1:
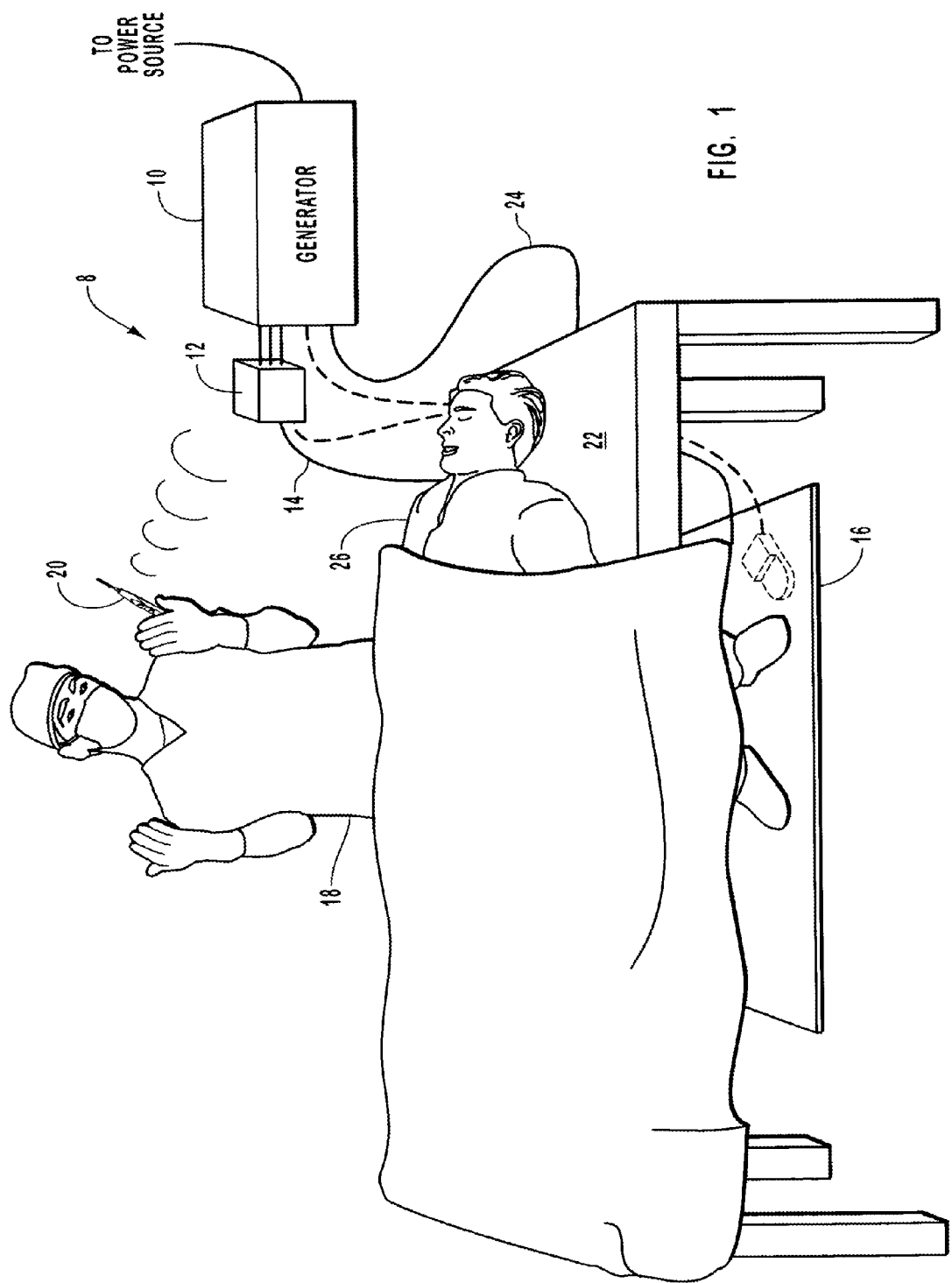
FIG. 1 is a schematic representation of one exemplary electrosurgical system according to one aspect of the present invention.

Referring now to FIG. 1, illustrated is an exemplary electrosurgical system, referenced by numeral 8. A physician may use this electrosurgical system 8 to perform electrosurgical procedures, such as cutting and/or coagulating tissue of a patient.

Further, the electrosurgical system 8 facilitates performance of electrosurgical procedures in safer environment for the patient, physician, and other participants in the procedure. Additionally, the configuration of system 8 allows the physician to perform electrosurgical procedures in a less strenuous manner than is possible with existing systems. As shown, system 8 includes an electrosurgical generator 10 that electrically communicates with a physician electrode 16 through use of an adapter 12. Alternatively, electrosurgical generator 10 may include the functionality of adapter 12 so that electrosurgical generator 10 may communicate with a physician electrode 16 via a connector 14.

Electrosurgical energy, such as radio frequency (RF) electrical energy created by electrosurgical generator 10 flows to electrosurgical instrument 20 through physician electrode 16 and from an electrosurgical instrument 20 through a patient electrode 22 to return to electrosurgical generator 10 via connector 24. The electrosurgical energy passes from physician electrode 16 to electrosurgical instrument 20 directly through a physician 18 manipulating electrosurgical instrument 20, and if we assume a sterile procedure, through a conductive glove worn by the physician 18, while the electrosurgical energy passes from electrosurgical instrument 20 to patient electrode 22 through a patient 26. In an alternate configuration, physician 18 may wear a surgical glove that includes one or more electrical traces adapted to cooperate with a pad attached to an arm of physician 18, the pad receiving the electrosurgical energy and transmitting the electrosurgical energy to the trace and hence to electrosurgical instrument 20. In another alternate configuration, the electrosurgical energy flows to electrosurgical instrument 20 through a combination of one or more of a conducting glove worn by physician 18, a conducting member incorporated within a gown worn by physician 18, through a single conductor extending from electrosurgical generator 10 and/or adapter 12 to electrosurgical instrument 20, or any other manner to provide an electrical connection between an electrosurgical generator and an electrosurgical instrument.

The electrosurgical energy produced by generator 10 is used to cut and/or coagulate tissue of patient 26. For instance, when electrosurgical generator 10 creates a constant sinusoidal signal deliverable to electrosurgical instrument 20, physician 18 may cut through tissue of patient 26. Alternatively, when electrosurgical generator 10 supplies a damped wave signal to electrosurgical instrument 20, physician 18 may coagulate leaking blood vessels. Further, when electrosurgical generator 10 transmits a combination of both a constant sinusoidal signal and a damped wave signal to electrosurgical instrument 20, physician 18 may concurrently cut and coagulate, thereby minimizing tissue trauma and blood loss during the surgical procedure.

The electrosurgical generator 10 may generate various operating frequencies of RF electrical energy and level of output power. The specific operating frequency and power output of electrosurgical generator 10 varies based upon the particular electrosurgical generator used and the needs of the physician during the electrosurgical procedure. The various frequencies and power levels associated with generator 10 are known to those skilled in the art.

Figure 2:
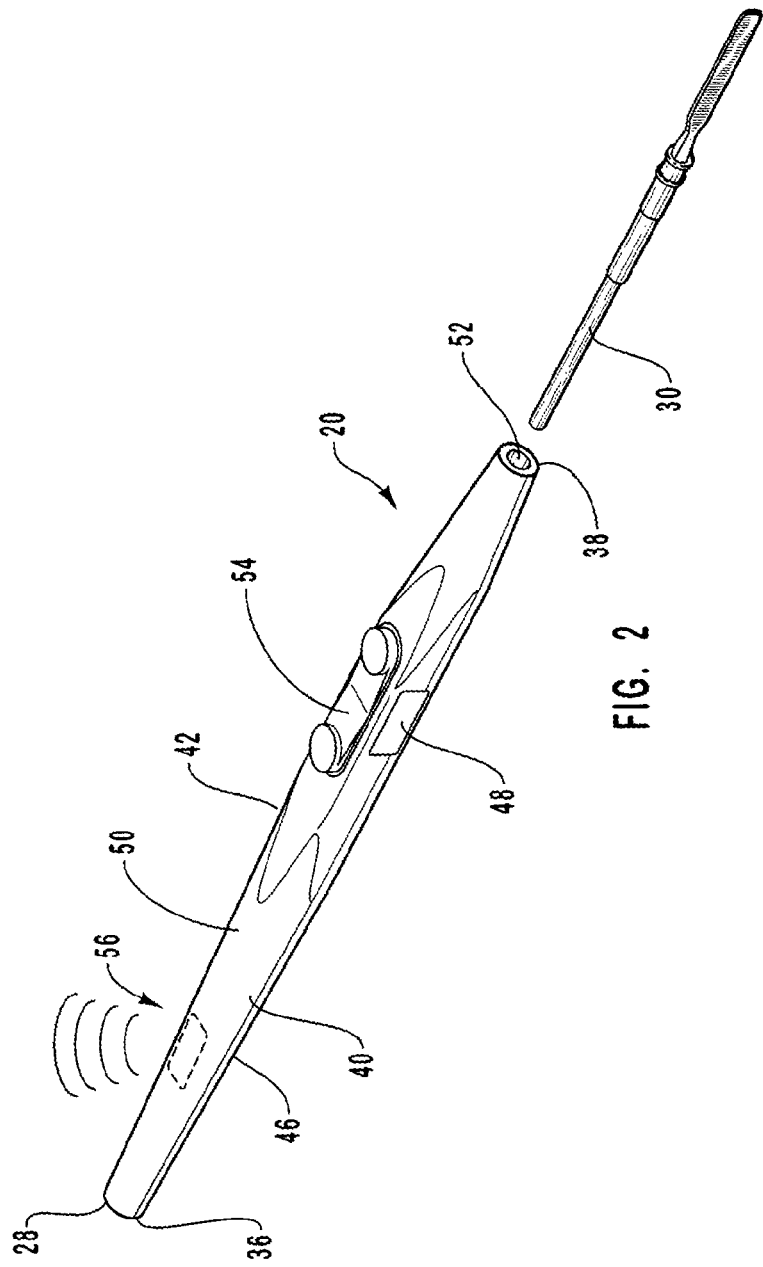
FIG. 2 is a perspective view of one electrosurgical instrument of the electrosurgical system of FIG. 1 in accordance with one aspect of the present invention.

During use of system 8, manipulation of electrosurgical instrument 20 initiates the delivery of electrosurgical energy from generator 10. When activated, electrosurgical instrument 20 introduces electrosurgical energy from generator 10 to tissue of patient 26. More specifically, as shown in FIG. 2, an electrode or tip 30 coupled to a hand piece 28 may introduce the electrosurgical energy to the body of patient 26. The combination of electrode or tip 30 and hand piece 28 forms an exemplary electrosurgical instrument 20.

The electrosurgical instrument 20, and more specifically tip 30, discharges the electrosurgical energy to patient 26 thereby causing heating of the patient's cellular matter that is in close contact with, adjacent to, or contiguous with tip 30. The current density is sufficient to cause a sufficiently high temperature rise to allow performance of electrosurgery by physician 18.

As shown in FIG. 2, hand piece 28 includes a proximal end 36 and a distal end 38. Disposed between proximal 36 and distal end 38 are one or more contacts 48, only one is shown in FIG. 2. The contacts 48 can be disposed on respective sides 40 and 42 of hand piece 28. These contacts 48 are electrically connected to tip 30 when the same is disposed within a recess 52 at distal end 38 of hand piece 28. By so doing, contacts 48 allow physician 18 to electrically connect generator 10 (FIG. 1) to tip 30 of electrosurgical instrument 20. For instance, with reference to FIG. 1, when physician 18 is to electrically conduct the electrosurgical energy created by generator 10, physician 18 directly touches both contacts 48 (FIG. 2) to allow the electrosurgical energy to pass to tip 30 (FIG. 2).

Alternatively, physician 18 may touch a single contact, such as when instrument 20 includes a single contact. In another configuration, physician 18 may use electrically conductive gloves to touch contacts 48 (FIG. 2), the conductive gloves contacting physician 18 or contacting an electrically conductive member attached to a gown or other clothing worn by physician 18.

Hand piece 28 may accommodate a variety of different electrodes or tips 30 that may be used for a variety of different purposes. For instance, tips may be used to cut tissue or coagulate blood vessels. The tips may be interchangeable or may be fixed to hand piece 28. Various tips are known to those skilled in the art.

Returning to FIG. 2, hand piece 28 includes an input device 54. Input device 54 controls the operating mode of electrosurgical instrument 20. In this illustrative configuration, input device 54 is a rocker switch that physician 18 manipulates to cause electrosurgical instrument 20 to function in cutting or coagulation mode. By activating input device 54 in one direction, electrosurgical instrument 20 functions to cut tissue of patient 26 (FIG. 1), while activating input device 54 in the opposite direction causes electrosurgical instrument 20 to function in the coagulation mode. Although reference is made to use of a rocker switch, it may be understood that any of a number of input devices may be used to initiate the cut and/or coagulation modes of electrosurgical instrument 20. For instance, input device 54 may be two buttons, one for cutting and one for coagulation. Alternatively, input device 54 may be a thumbwheel type switch, or other type of input device that is capable of allowing a physician to select between two or more operating modes of the electrosurgical instrument. In another configuration, input device 54 is moved from instrument 20, while the input device communicates with instrument 20 to initiate delivery of electrosurgical energy. For instance, the input device may have the form of a foot activated input device, as illustrated in dotted lines in FIG. 1, which includes one or more foot pedals that allow a physician, clinician, or operator to initiate and terminate delivery of electrosurgical energy to tip 30 (FIG. 2) of electrosurgical instrument 20. The foot activated input device may be either physically or wirelessly connected to adapter 12 and/or generator 10. In still another configuration, either an input device mounted to the instrument or a remote input device may operate the electrosurgical instrument.

As physician 18 manipulates input device 54 (FIG. 2), a transmitter 56 (FIG. 2) of electrosurgical instrument 20 delivers a wireless signal to adapter 12 or generator 10 initiating the delivery of the particular electrosurgical energy selected by physician 18. Stated another way, when physician 18 selects cutting mode for electrosurgical instrument 20 through moving input device 54 (FIG. 2) in one direction transmitter 56 (FIG. 2) delivers a wireless signal indicative of a request for electrosurgical energy having a constant sinusoidal form. In contrast, when physician 18 selects coagulation mode for electrosurgical instrument 20 through moving input device 54 (FIG. 2) in another direction, transmitter 56 (FIG. 2) delivers a wireless signal indicative of a request for electrosurgical energy having a damped wave signal.

The transmitter 56 (FIG. 2) may deliver a wireless signal to adapter 12 or generator 10. The wireless signal may have one of a variety of different wavelengths of electromagnetic energy. Alternatively, the wireless signal may alternate between one or more different wavelengths of electromagnetic energy. As used herein, the term "wireless signal" refers to a signal delivered using technology that delivers signals without use of a conductive wire or optical fiber that extends between a first device and a second device that is to receive a signal. Consequently, transmitter 56 (FIG. 2) may deliver the "wireless signal" using electromagnetic radiation having an infrared wavelength, a microwave wavelength, a radio wavelength, or any other electromagnetic radiation wavelength that may be used to send one or more control signals to an electrosurgical generator without the use of a conductive wire or optical fiber as the medium for carrying the signal.

As mentioned above, the electrosurgical energy generated by generator 10 is transmitted from generator 10 to tip 30 though hand piece 28 of the electrosurgical instrument 20 illustrated in FIG. 2. This delivery of electrosurgical is accomplished, in one embodiment and with continued reference to FIG. 1, through use of connector 14, physician electrode 16, and optionally physician 18. According to the exemplary embodiment of the present invention as depicted in FIG. 1, disposed between electrosurgical generator 10 and physician 18 are connector 14 and physician electrode 16. Similarly disposed between electrosurgical generator 10 and patient 26 are connector 24 and patient electrode 22.

Each connector 14 and 22 is permanently or temporarily connected to respective electrodes 16 and 22 and/or electrosurgical generator 10. Although both connectors 14 and 22 may have similar configuration, one skilled in the art may understand that connectors 14 and 22 may have different configurations so long as connectors 14 and 22 perform the desired function of transmitting electrosurgical energy. Therefore, each end of each connector may include means for coupling the connector to either the electrosurgical generator or the electrode, such as but not limited to, clamps, threaded insertable elements, or any plug capable of transmitting electrosurgical energy, such as but not limited to, a) banana plug, a phone jack, an Ethernet jack, a coaxial connector, or the like. Further, although illustrative structures capable of performing the functions of means for coupling the connector to the electrosurgical generator or the electrode, one skilled in the art in light of the teaching contained herein may identify various other structures capable of performing the desired functions.

In this exemplary embodiment, physician electrode 16 delivers electrosurgical energy, such as RF signals and current, from generator 10, through physician 18, to electrosurgical instrument 20, while electrode 22 returns or provides a return path for the electrosurgical energy from patient 26 to generator 10. The electrosurgical electrical energy from electrosurgical generator 10 is delivered to physician electrode 16 when physician 18 activates input device 54 (FIG. 2) of electrosurgical instrument 20 during an electrosurgical procedure. For instance, upon physician 18 selecting to cut tissue of patient 26, transmitter 56 (FIG. 2) delivers a signal to generator 10 causing delivery of current having a constant sinusoidal form typical of generator cut modes to electrosurgical instrument 20 through connector 14, physician electrode 16, and physician 18. The electrosurgical energy passes through patient 26 to return to electrosurgical generator 10 through patient electrode 22 and connector 24.

In this particular configuration, both physician electrode 16 and patient electrode 22 prevent physician 18 and patient 26 from being burned as the electrosurgical energy passes through physician 18 and patient 26 during the electrosurgical procedure. As discussed previously, when the area of an individual, such as the physician or patient, contacting a return electrode is sufficiently small that the current density of the signals exceeds 100 milliamperes per square centimeter, the individual may be burned during the electrosurgical procedure. Since the electrosurgical current, is constant throughout the electrical circuit of the electrosurgical system, the same current density limit is applicable to the contact area of physician 18 standing upon physician electrode 16 during an electrosurgical procedure and patient 26 resting upon patient electrode 22. Therefore, it is desirable that the contact area of physician 18 upon physician electrode 16 and patient 26 on patient electrode 22 is large enough that the current density is lower than 100 milliamperes per square centimeter.

Various manners are known to achieve this desired level of current density. For instance, in one configuration, each electrode 16 and 22 is covered in a conductive gel that aids with maintaining a sufficiently large contact area of physician 18 and/or patient 26 with respective electrodes 16 and 18. In another configuration, any other return electrode technology may be used to achieve the desired current density. For instance, and not by way of limitation, a metal plate and gel may be used to achieve the desired current density, while in another configuration a current limiting capacitive pad may be used to achieve the desired current density. In another configuration, each physician electrode 16 and patient electrode 22 is self-limiting.

Self-limiting refers to the ability of an electrode to prevent current flowing through an electrode when the contact area of an individual upon the electrode drops below a threshold level, below which the individual would receive a burn. The various properties and characteristics of an electrode that is self-limiting are disclosed in U.S. Pat. No. 6,454,764, issued Sep. 24, 2002, and entitled "Self-limiting Electrosurgical Return Electrode," U.S. Pat. No. 6,083,221, issued Jul. 4, 2000, and entitled "Resistive Reusable Electrosurgical Return Electrode," U.S. patent application Ser. No. 08/741,468, filed Oct. 30, 1996, and entitled "Reusable Electrosurgical Return Pad," U.S. patent application Ser. No. 09/769,025, filed Jan. 24, 2001, and entitled "Capacitive Reusable Electrosurgical Return Electrode", U.S. Pat. No. 6,214,000, issued Apr. 10, 2001, and entitled "Capacitive Reusable Electrosurgical Return Electrode", and U.S. Pat. No. 6,053,910, issued Apr. 25, 2000 and entitled "Capacitive Reusable Electrosurgical Return Electrode," the disclosures of which are incorporated by this reference. Although the above-identified self-limiting electrodes are typically discussed as return electrodes, such as is applicable with patient electrode 22, the same electrodes may be used as physician electrode 16 to prevent burning of physician 18.

Generally, the self-limiting characteristics or properties of physician electrode 18 and/or patient electrode 22 occur as the contact area between physician 18 and physician electrode 18 and/or patient 26 and patient electrode 22 is reduced to a small contact area. At some point of reduction in contact area between physician 18 and physician electrode 18 and/or patient 26 and patient electrode 22, the effective impedance (from all resistive, capacitive, and/or inductive components) rises to a level relative to the impedance presented at the site of electrosurgical instrument 20. This rise in impedance diminishes the electrosurgical effect of electrosurgical instrument 20 or otherwise prevents effective use of instrument 20 by physician 18, thus signaling physician 18 that physician 18 and/or patient 26 should be repositioned so as to present a greater surface area in contact with respective physician electrode 16 and/or patient electrode 22. At the same time, the total circuit impedance would be increased so that the total current that would flow if physician 18 attempted to employ electrosurgical instrument 20 without repositioning himself/herself and/or patient 22 would be reduced to a value below that which would cause undesired trauma to patient 22.

As disclosed in the above applications and patents, the interrelationship of various parameters that affect self-limiting is defined by:

$$t = \frac{1.2A(75\beta)\sqrt{1+\omega^2\rho^2\kappa^2\varepsilon_0^2}}{\rho} \quad (1)$$

where variable t is the thickness of the electrodes in centimeters (cm) and $\kappa$ is the dielectric constant of insulating material forming part of the electrode or disposed between the conductive portion of the electrode and the patient and/or physician, such as but not limited to clothes, sheets, footwear, bedding, or other materials that may be disposed between physician electrode 16 and physician 18 and/or patient electrode 22 and patient 26. The variable $\beta$ is the total impedance divided by the AAMI standard (75 ohms), the variable $\omega$ is the angular frequency of electrosurgical generator in radians per second (radians/sec), and variable $\rho$ is the bulk resistivity in ohmns per centimeter ($\Omega\cdot$cm). The variable A is the electrode area in square centimeters (cm$^2$) and the variable $\in_o$ is the electrical permittivity constant in Farads per centimeter (F/cm).

Using Equation 1, the maximum electrode thickness may be approximately from about 0.5 to about 4 inches (about 1.3 cm to about 10.2 cm) and more preferably about 1 inch thick (about 2.5 cm), where $\kappa=5$. Above these thicknesses, electrodes 16 and 22 may become unwieldy to use and uncomfortable for physician 18 or patient 22. Thus, to be self-limiting, the minimum bulk resistivity for electrode 16 and/or 22 of such thickness is about The preceding equation is representative of the bulk resistivity required for electrodes 16 and/or 22 to be self-limiting. It may be appreciated, however, that similar equations may be identified and used to obtain the necessary self-limiting impedances for electrodes modeled using primarily capacitive or inductive components, or combinations of resistive, capacitive, and/or inductive components. Therefore, following is a discussion of the self-limiting requirements for the bulk impedance of electrode 16 and/or 22, whether such impedance arises from resistive, capacitive, and/or inductive components of impedance.

The self-limiting behavior of the electrode of the present invention results from the existence of sufficient return impedance to make an electrode site burn impossible when the area of contact between the patient and/or physician and the electrode is substantially reduced. Based upon Association for the Advancement of Medical Instrumentation ("AAMI") standards, normal electrosurgical currents are about 500-700 mA. If we assume for safety, that the maximum electrosurgical current is 1000 mA and the current density must be kept below 100 mA/cm$^2$, in accordance with test results of the Emergency Care Research Institute, a well-known medical testing agency, then the minimum safe contact area is 10 cm$^2$.

In general, this requirement may be met with any number of electronic components hooked together in various configurations, including series and parallel combinations of capacitors, resistors, and even inductors, provided that the total impedance presented by the resulting circuit be about 75$\beta$ or greater when the contact area is reduced to 10 cm$^2$, where $\beta$ is defined by:

$$\beta = \frac{Z_{tot}}{75\Omega} \quad (2)$$

where $Z_{tot}$ is the total impedance of the electrosurgical electrode.

Defining the total impedance of the circuit between the electrode of the electrosurgical generator and the patient or physician as $Z_{TOT}$. This impedance is generated by the capacitive, resistive, and inductive properties of the materials inserted between the patient or physician and the respective electrodes. We define the "bulk impedance" of the material a volume independent measure of the impedance of the material, that is frequency dependent, as:

$$\eta = \frac{(A)(Z_{TOT})}{t} \quad (3)$$

Here A is the area of the material and t is the thickness of the material. This is analogous to the relationship between the volume dependent ohmic resistance R and the related volume independent characteristic of the resistive material called the "bulk resistivity" $\rho$.

One manner to describe the self-limiting requirement is expressed in terms of:

$$|Z_{TOT}| = \frac{t|\eta|}{A} > 75\beta \quad (4)$$

Or therefore $$|\eta| > \frac{(75\beta)A}{t} \quad (5)$$

If we use the minimum contact area of 10 cm$^2$ (about 1.55 inch$^2$) identified previously, with $\beta=10$, t=1 inch (about 2.5 cm), and a factor of 1.2 to account for edge effects to find that for a pure resistive electrosurgical electrode, $$|\eta| > 4000 \Omega\cdot cm \quad (6)$$

Therefore, in the purely resistive case, the bulk impedance ($\eta$) is identified as the bulk resistivity ($\rho$) of the conducting material in the electrode. The results in Equation 6, however, generalize to all materials and electrical components, including resistive, capacitive, and inductive components, and any combinations thereof. As long as the bulk impedance of the electrosurgical electrode is greater than 4000 Ω·cm, the electrode will be self-limiting, regardless of whether the self-limiting behavior is due to, one or more of, resistive, capacitive, or inductive impedance.

Generally, when electrode 16 and/or 22 are of a self-limiting type described above and in the above-identified pending patent applications and issued patents, such electrodes 16 and/or 22 do not need to be in direct contact with the physician or patient, either directly or through intervening conductive or nonconductive gel. In addition, because of the expansive size of physician electrode 16 or patient electrode 22, there is no need for tailoring electrodes 16 and 22 to fit physical contours of the physician or patient. It has been found that although with selected materials and geometries, the self-correcting and self-limiting principles may be achieved in an electrode as small as about seven square inches (or about 45 square centimeters) in working surface area, the preferable range of exposed upper working surface area of electrodes 16 and 22 lies in the range of from about 11 to 1,500 square inches (or about 70 to 9,680 square centimeters). By making each electrode 16 and several times larger (typically, at least an order of magnitude larger) in working surface area than previous electrodes, the need for direct physical attachment to the physician or patient, either directly to the skin or through gels, is eliminated.

Moreover, although electrodes 16 and 22 are depicted as being rectangular, it will be evident that they could be oval or contoured as, for example, to follow the silhouette of the torso or other part of the body of a patient. As will be evident from the foregoing, any type of electrode may be used as physician electrode 16 or patient electrode 22, so long as the electrode is configured so that when the electrode is used: (1) the current density on the surface of the patient or physician is sufficiently low; (2) the electrical impedance between the electrode and the patient or physician is sufficiently low so that electrical energy is not concentrated sufficiently to heat the skin of the patient at any location in the electrical return path by more than six degrees)(6°) Celsius; and (3) the characteristics of the materials and geometries are such that if the effective area of the electrode is reduced below a selected threshold level, there will be insufficient energy dissipated at the surgeon's implement for him to continue effectively using the implement in its electrosurgical mode.

Each electrode 16 and 22 may be made of conductive plastic, rubber, or other flexible material which, when employed in the electrode will result in an effective impedance of equal to or greater than approximately 4000 Ω·cm. Silicone or butyl rubber has been found to be particularly attractive materials as they are flexible, as well as readily washable and sterilizable. Alternatively, the main body of the electrode may be made of inherently relatively high resistance flexible material altered to provide the requisite conductivity. A preferred example of the latter is that of silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors. Further, each electrode 16 and/or 22 may include a pressure sore pad, cushioning, heating or cooling functions, combinations thereof, or the like to prevent injury to physician 18 and/or patient 26.

Figure 3:
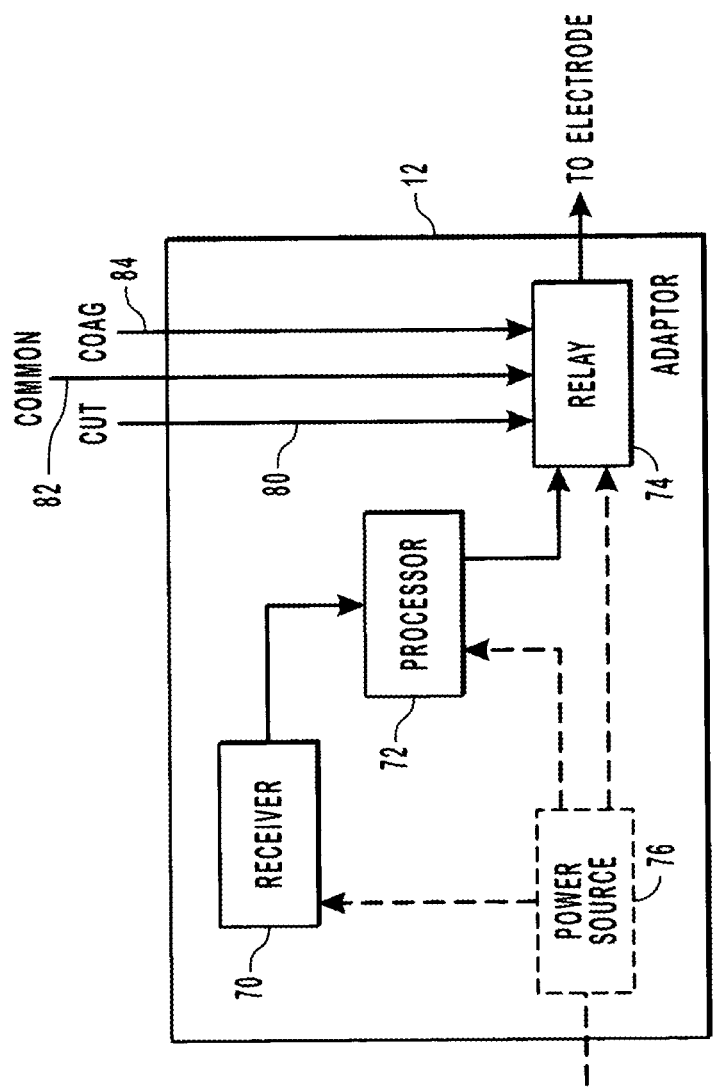
FIG. 3 is a schematic representation of an adapter of the electrosurgical system of FIG. 1 in accordance with one aspect of the present invention.

Referring now to FIG. 3, depicted is a schematic representation of adapter 12, according to one embodiment of the present invention. Adapter 12 acts as intermediary between generator 10 (FIG. 1) and physician electrode 16 (FIG. 1). Adapter 12, in this configuration, receives signals from electrosurgical instrument 20 (FIG. 1) that represent selections made by the physician for particular electrosurgical energy from generator 10 (FIG. 1). In response to receiving these control signals, adapter 12 initiates the delivery of electrosurgical energy consistent with control signals to electrosurgical instrument 20 (FIG. 1) through physician 18 (FIG. 1).

As illustrated, adapter 12 includes a receiver 70 that cooperates or is complimentary to transmitter 56 (FIG. 2) in electrosurgical instrument 20 (FIG. 2). Receiver 70 receives wireless signals from transmitter 56 (FIG. 2) that indicate or dictate the particular mode of operation of electrosurgical instrument 20 (FIG. 2). In this illustrative configuration, receiver 70 receives infrared radiation carrying the control signals. In alternate configurations, receiver 70 may receive any wavelength of electromagnetic radiation that carries the control signals.

The signal identified by receiver 70, is delivered to processor 72 for analysis and to identify the particular mode of operation for electrosurgical instrument 20 (FIG. 2), such as but not limited to cutting mode, coagulating mode, or a combination of both cutting and coagulating. Processor 72 utilizes the signal to cause one or more relays 74 to deliver the appropriate wavelength and/or waveform of electrosurgical energy to electrosurgical instrument 20 (FIG. 2). For example, in one configuration, relays 74 receive three electrical lines from generator 10 (FIG. 2); a cut line 79, a common line 81, and a coagulation line 83. Cut energy or signals are delivered along cut line 79, while coagulation energy or signals are delivered along coagulation line 83. The common line 81 helps maintain generator 10 (FIG. 2) and adapter 12 at the same potential.

Multiple relays may be used in association with relays 74 to deliver the appropriate electrosurgical signal to electrosurgical instrument 20. Further, although reference is made to processor 72 and relays 74 being separate elements that communicate one from the other, it may be understood by one skilled in the art in light of teaching contained herein, that relays 74 may be incorporated within the functionality of processor 72, resulting in processor 72 controlling the delivery of electrosurgical signals to electrosurgical instrument 20.

As illustrated in FIG. 3, adapter 12 may further include a power source 76. Power source 76 may be solely included within adapter 12 or alternatively, power may be delivered to adapter 12 via the signals received from generator 10 (FIG. 2). In another configuration, a separate power source provides power to both adapter 12 and generator 10 (FIG. 2). Various power sources are known to those skilled in the art in light of the teaching contained herein.

Referring now to FIG. 4, depicted is a schematic representation of portions of an interior of electrosurgical instrument 20 in accordance with one embodiment of the invention. As shown, electrosurgical instrument 20, and more specifically hand piece 28, includes transmitter 56 disposed with an interior thereof. Connected to transmitter 56 is a power supply 80 that provides electrical energy, such as electrical current and voltage to operate or power transmitter 56. In electrical communication with transmitter 56 is input Input device 54, in this configuration, includes a movable member 82 that may be manipulated by physician 18 (FIG. 1) during a surgical procedure. The movable member 82 is adapted to touch contacts 84 and 86 that respectively initiate cutting or coagulating operation of electrosurgical instrument 20. Contacts 84 and 86 may be one of a variety of different types of contact associated with a switch, such as but not limited to, a dome switch, a membrane switch, an optical switch, a mechanical switch, or other switch that is adapted to send a signal upon operating the input device.

Upon manipulation of movable member 82 in one direction, a circuit is formed that allows current to flow, thereby causing transmitter 56 to deliver a particular signal indicating that the physician has selected to deliver a particular waveform of RF energy or electrosurgical energy to patient 26 (FIG. 1). In this manner, a physician 18 (FIG. 1) may select a particular operational mode for electrosurgical instrument 20. Although transmitter 56 is depicted as being at proximal end 36, it may be understood that transmitter 56 may be disposed at distal end 38 or at any location between proximal end 36 and distal end 38. Similarly, power supply 80 may be disposed between or at proximal end 36 and distal end 38. Further, alternative configurations of input device 54 may vary the number of contacts and interrelationships between the various components of the electrosurgical instrument. For instance, when input device 54 has the form of a single button with a double dome switch, activation of the switch may first form a current signal and completing activation to a second circuit that activates the coagulation signal.

Figure 6:
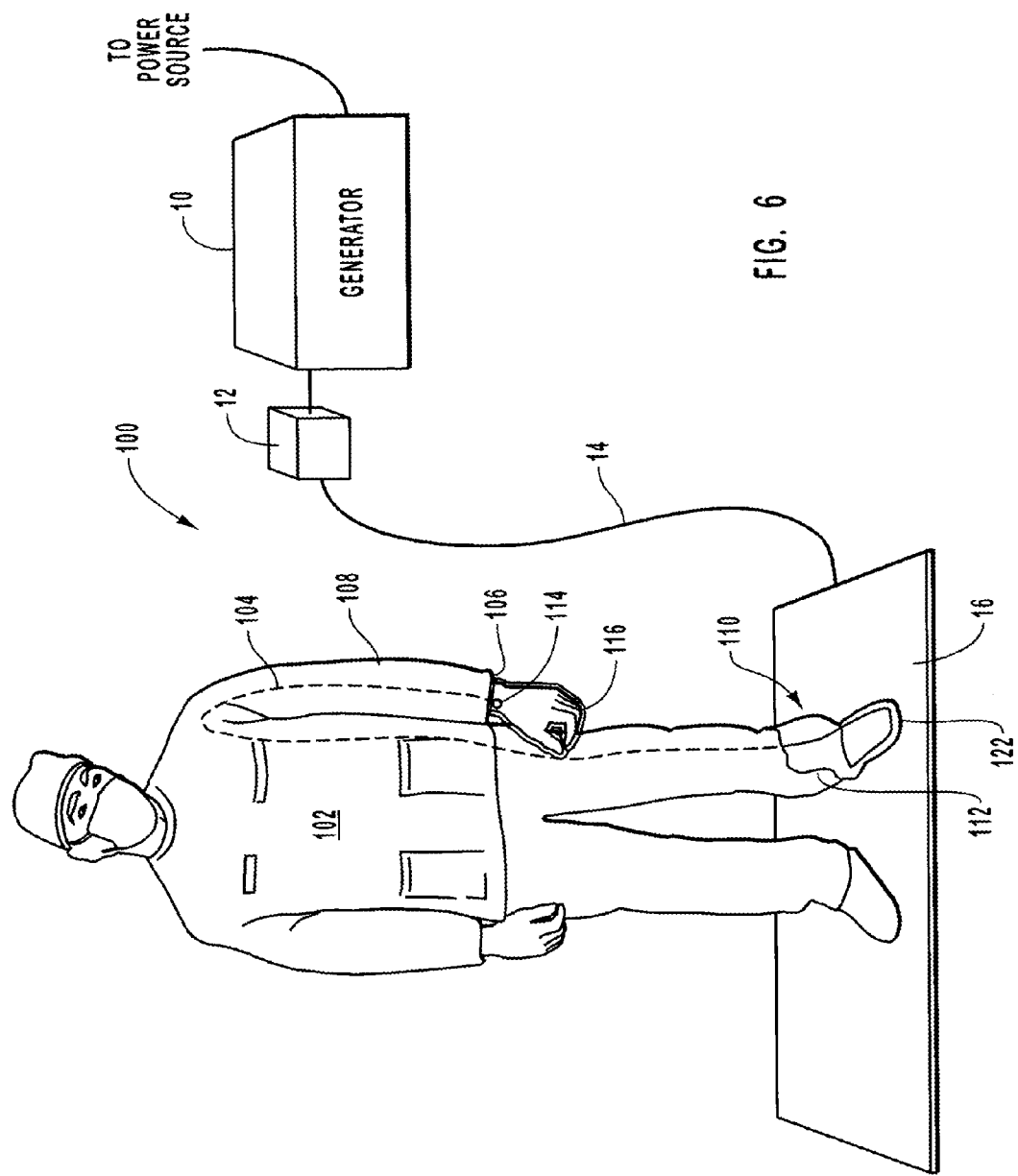
FIG. 6 is a schematic representation of another exemplary electrosurgical system according to one aspect of the present invention.

Referring now to FIGS. 5 and 6, upon activating input device 54 to deliver electrosurgical signal energy to electrosurgical instrument 20, the electrosurgical energy is delivered to physician electrode 16 (FIG. 6) and through physician 18 to contacts 48 (FIG. 5), only contact 48 being depicted in FIG. 5. One or both of the contacts 48 electrically communicate with recess 52, or more specifically to one or more conductive members 90 disposed within recess 52 to make electrical connection with an electrosurgical tip, depicted in dotted lines. Contacts 48 may be any conductive member that allows electrical signals and/or electrical currents to flow therethrough. For instance, each contact may be a metallic member, a composite member, capacitive member, or any other conductive member. Furthermore, each contact may be adapted to cooperate with a complementary contact formed in a glove worn by the physician, clinician, or operator of instrument 20. In this regard, contacts 48 may be configured to receive or mate with at least one complementary contact formed in the glove. In another configuration, each contact snap fits or friction fits with a complementary contact formed or coupled to the glove. In addition to the above, contacts 48 may have various other configurations. For instance, and not by way of limitation, each contact may completely or partially extend from a distal end of instrument 20 toward a proximal end thereof, and vice versa. Additionally, each contact may cover all or a portion of side 40 and 42 respectively and/or all or a portion of the top or bottom of instrument 20. Furthermore, instrument 20 may include a single contact that extends from side 40 to 42, or vice versa. In still another configuration, instrument 20 acts as a contact, with instrument 20 including a contact that complete covers or forms an outer surface of instrument 20. In yet another configuration, hand piece 28 of instrument 20 is the contact, i.e., hand piece 28 of instrument 20 being conductive.

The electrosurgical instrument 20 is adapted to deliver control signals to the electrosurgical generator to initiate delivery of electrosurgical energy. This electrosurgical instrument is not tied or tethered to the electrosurgical generator through the conductor cord. Therefore, the electrosurgical instrument may be freely used by the physician without a restrictive cord limiting the movement of the instrument. Consequently, the electrosurgical instrument allows a physician to perform electrosurgical procedures in a less strenuous manner than is currently possible. Further, by eliminating the cord between the instrument and generator, a safer environment is created for use of electrosurgical instruments and performance of electrosurgical procedures. In an alternate configuration, foot controls, as depicted in dotted form in FIG. 1, may initiate delivery of electrosurgical energy to the electrosurgical instrument. The manner by which the foot controls may initiate delivery of electrosurgical energy may be similar to the manner by which electrosurgical instrument 20 initiates delivery of electrosurgical energy. For instance, the foot controls may utilize various switches to deliver the detector signal to the electrosurgical generator and/or the adapter.

Referring now to FIG. 6, depicted is an alternate configuration of the present invention. In this particular configuration, electrosurgical energy passes to electrosurgical instrument 20 (FIG. 5) via an electrosurgical path external to the physician. In this way, electrosurgical energy flows through a path created in the clothing of the physician. Although delivery of the electrosurgical energy is performed in a different manner to that described with respect to FIG. 1, this illustrative configuration still allows delivery of wireless signals without the need for a physical control path between the electrosurgical generator and the electrosurgical instrument. Therefore, the system depicted in FIG. 7 also eliminates the need for control lines and electrical communication lines directly between the electrosurgical generator and the electrosurgical instrument. Consequently, the methods, systems, and instruments alleviate the problems associated with corded electrosurgical instruments and allow a physician to perform electrosurgical procedures in a less strenuous manner within a safer environment than is currently the case.

As illustrated, a system 100 includes a gown 102, such as a sterile gown, that includes an electrical trace 104 extending substantially from a distal end 106 of a sleeve 108 toward a distal end 110 of a leg 112. Trace 104 may be fabricated from various materials so long as trace 104 is capable of transmitting electrosurgical energy, current, or RF signals. For instance, and not by way of limitation, trace 104 may be fabricated from a metallic substance, a composite material, or any other suitable material or combination of materials that are capable of conducting electrosurgical energy.

Figure 7:
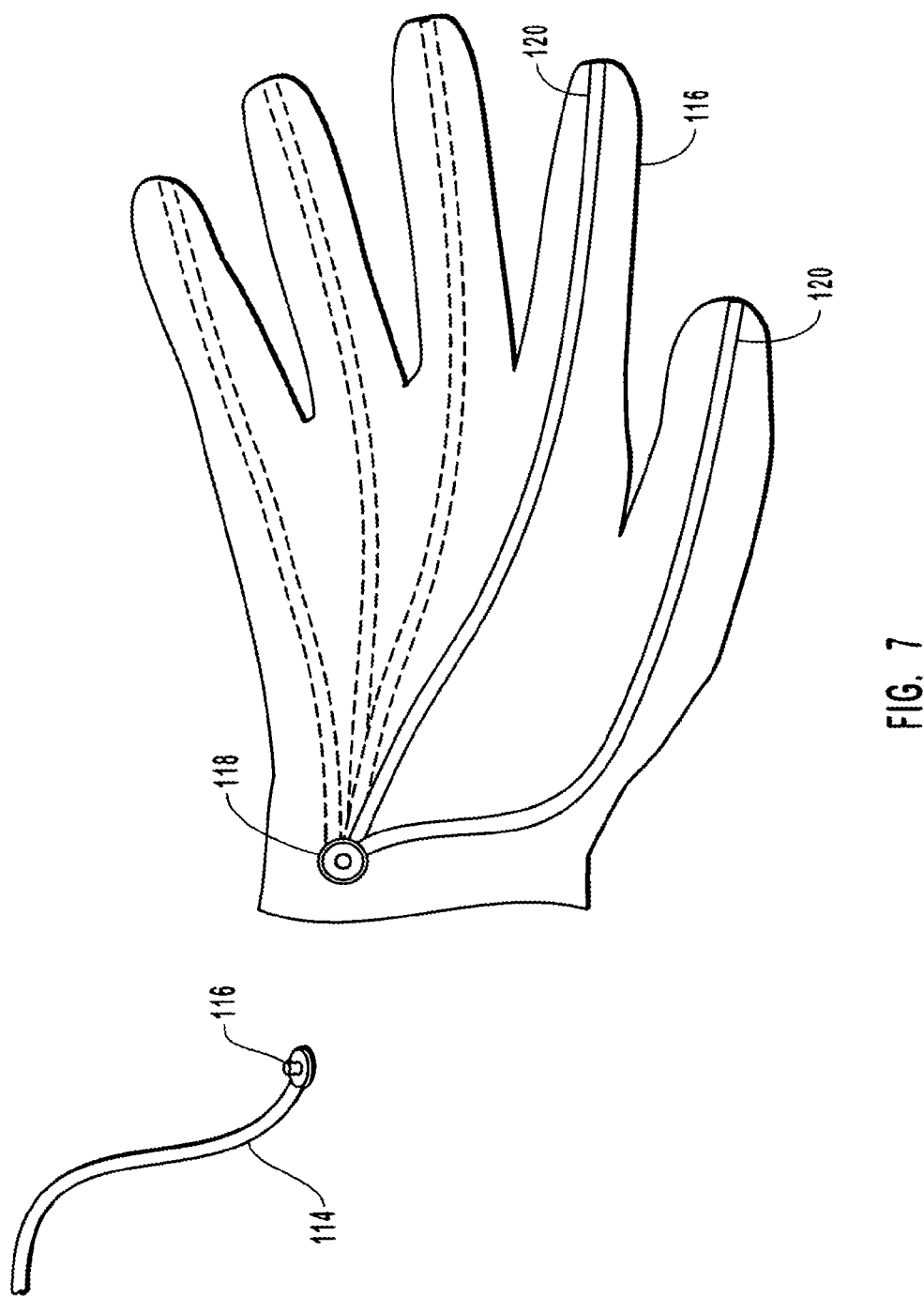
FIG. 7 is a schematic representation of a conductive glove associated with the electrosurgical system of FIG. 6.

The trace 104 terminates at a distal end thereof in a connector 114, as shown in FIG. 7. Connector 114 is adapted to cooperate with a complementary connector 118 formed on conductive glove 116. Alternatively, connector 114 may be adapted to cooperate directly with instrument 20 (FIG. 5), such that electrosurgical energy is delivered directly to instrument 20 (FIG. 5) from trace 104. Connector 114 may, therefore, be any type of connector that is capable of making an electrical connection, such as a snap fit, male/female connection, conductive hook and loop fastener, or other suitable connection for creating an electrical connection, so long as the same may cooperate with complementary connector 118 associated with conductive glove 116 and/or a complementary connector associated with instrument 20 (FIG. 5).

Conductive glove 116 may include one or more conductive members 120 that attach to or are otherwise formed with the remainder of glove 116. One such conductive glove is illustrated in U.S. Pat. No. 3,845,771, the disclosure of which is incorporated herein by this reference. Alternatively, conductive glove 116 may be fabricated from any electrically conductive material, such as but not limited to, conductive filled silicon, conductive filled latex, combinations thereof, or any other materials or structures capable of conducting electrosurgical energy or signals. In this case, conductive glove 116 need not include conductive members 120.

Referring again to FIG. 7, trace 104 terminates at proximal end at a conductor member 122. Although reference is made to trace 104 terminating at a proximal end thereof at conductor member 122, one skilled in the art may appreciate that trace 104 may terminate in contact with connector 114, such that electrosurgical energy may be delivered directly to trace 104 from connector 114.

In the illustrated configuration, conductor member 122 receives electrosurgical energy from physician electrode 16. The conductor member 122 may be formed in removable footwear of the physician, a removable covering for the physician's footwear, combinations thereof or other members, so long as conductor member may make contact with or sufficiently spaced apart from physician electrode 16 to allow electrosurgical energy to flow therethrough. For instance, instead of a single conductor 122, it may be understood that multiple conductor members may be used at proximal end of trace 104. Similarly, multiple connectors 114 may be used to connect a distal end of trace to conductive glove 116.

In an alternate configuration of the system illustrated in FIG. 6, a system of the present invention may utilize a conductive glove, similar to conductive glove 116, without the need for trace 104 formed in gown 102. In this configuration, the physician continues to conduct the electrosurgical signals from generator 10, while conductive glove 116 on one hand provides additional conductive surface for the current to flow to contacts 48, of electrosurgical instrument 20 (FIG. 2). In this alternative configuration, the physician may include an insulative glove on the opposite hand to prevent shorting of the system and inadvertent contact of the patient with two conductive members, potentially resulting in burns to the patient and/or the physician.

The configuration of the present invention described refers to FIGS. 6 and 7, also enables a physician to perform electrosurgical procedures in a less strenuous manner than is currently possible. Further, the illustrated system allows for wireless signals to be delivered from the electrosurgical instrument to the electrosurgical generator, thereby eliminating the need for a direct physical control signal path between the electrosurgical generator and the electrosurgical instrument, that is typically included as a member capable of transmitting or delivering the control signals along a wire or an optical fiber from the electrosurgical instrument to the electrosurgical generator. In this manner, the system creates a safer environment for the physician to perform electrosurgical procedures and allows the physician greater movement in performing the procedures.

Figure 8:
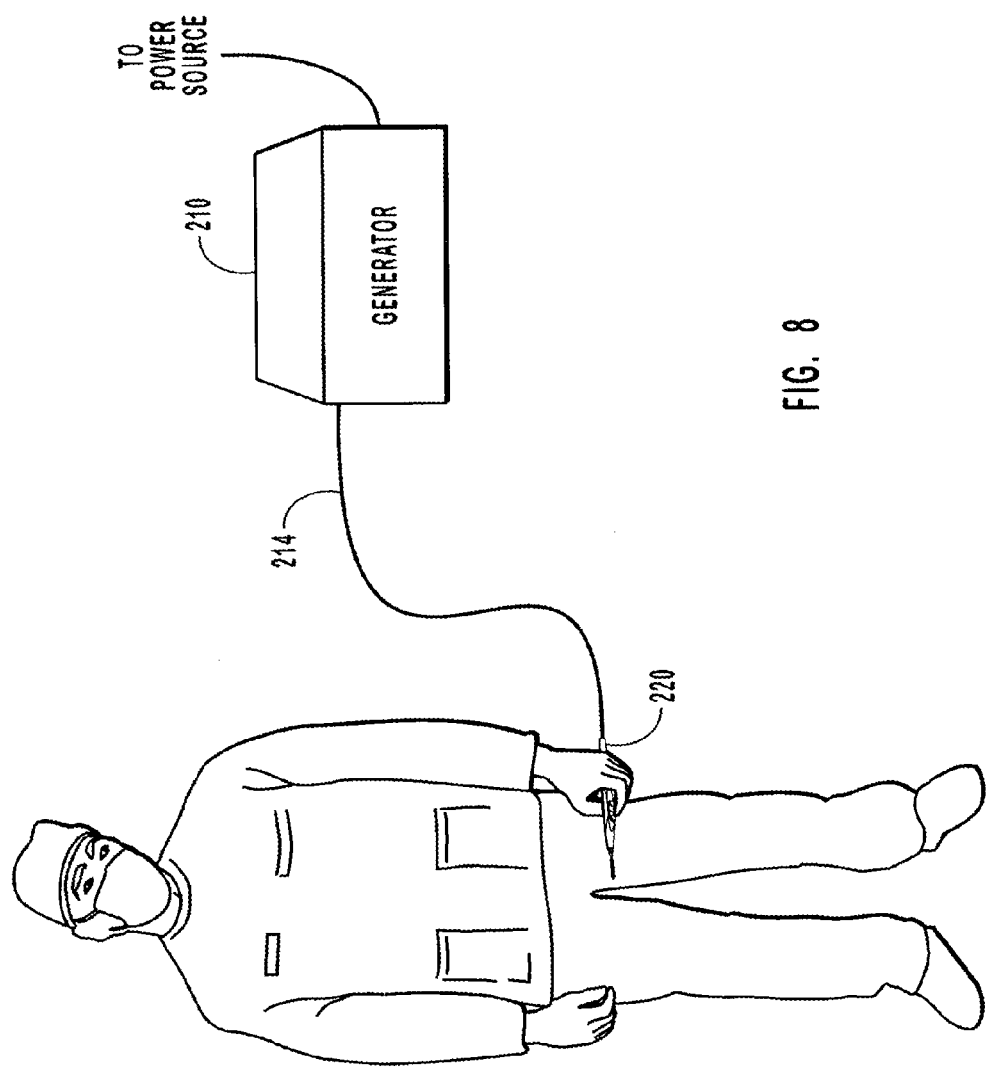
FIG. 8 is a schematic representation of yet another exemplary electrosurgical system according to one aspect of the present invention.

Referring now to FIG. 8, depicted is another embodiment of the present invention. Structures of this embodiment that are similar to those previously discussed will be designated with similar reference numerals. This embodiment may initiate delivery of electrosurgical energy without the need for a physical control path between the electrosurgical generator and the electrosurgical instrument. Rather, wireless control signals are used to initiate delivery of electrosurgical energy to the electrosurgical instrument. The electrosurgical energy is conducted along a conductor that extends from the electrosurgical generator to the electrosurgical instrument.

Therefore, the methods, systems, and instruments of this presently described embodiment eliminate the need for a control line between the electrosurgical generator and the electrosurgical instrument. Consequently, the methods, systems, and instruments of this embodiment alleviate the problems associated with corded electrosurgical instruments and allow a physician to perform electrosurgical procedures in a less strenuous manner than is currently possible.

As illustrated, an electrosurgical system 200 is depicted. The system 200 includes an electrosurgical generator 210 that may have a similar configuration to the other electrosurgical generators described herein. Therefore, electrosurgical generator 210 may receive wireless signals from an electrosurgical instrument 220 to initiate delivery of RF signals or electrosurgical energy from electrosurgical generator 210 to electrosurgical instrument 220. In this regards, electrosurgical generator 210 may include the functionality and/or structure associated with adapter 12 (FIG. 1).

Figure 9:
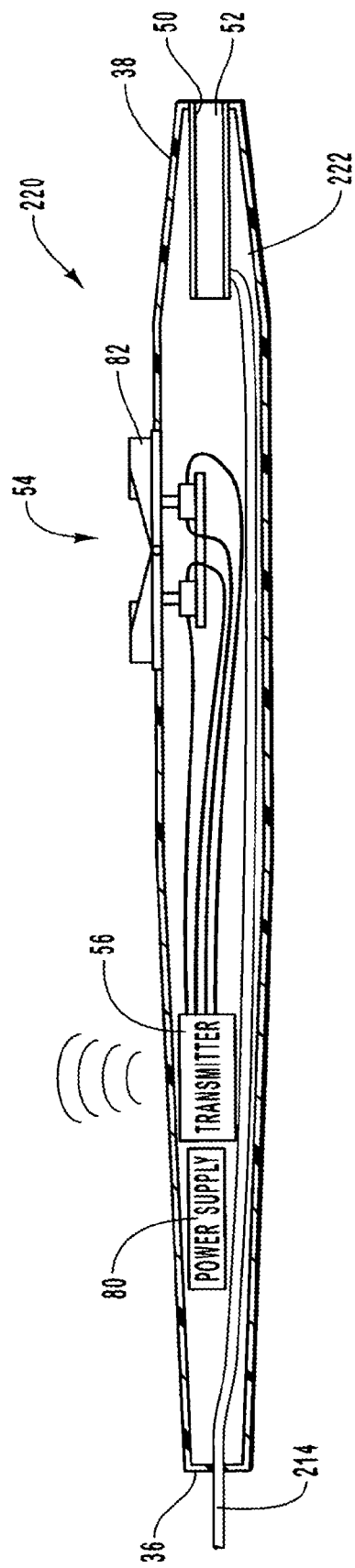
FIG. 9 is a schematic representation of a cross-sectional side view of an electrosurgical instrument of FIG. 8 in accordance with one aspect of the present invention.
Figure 3:
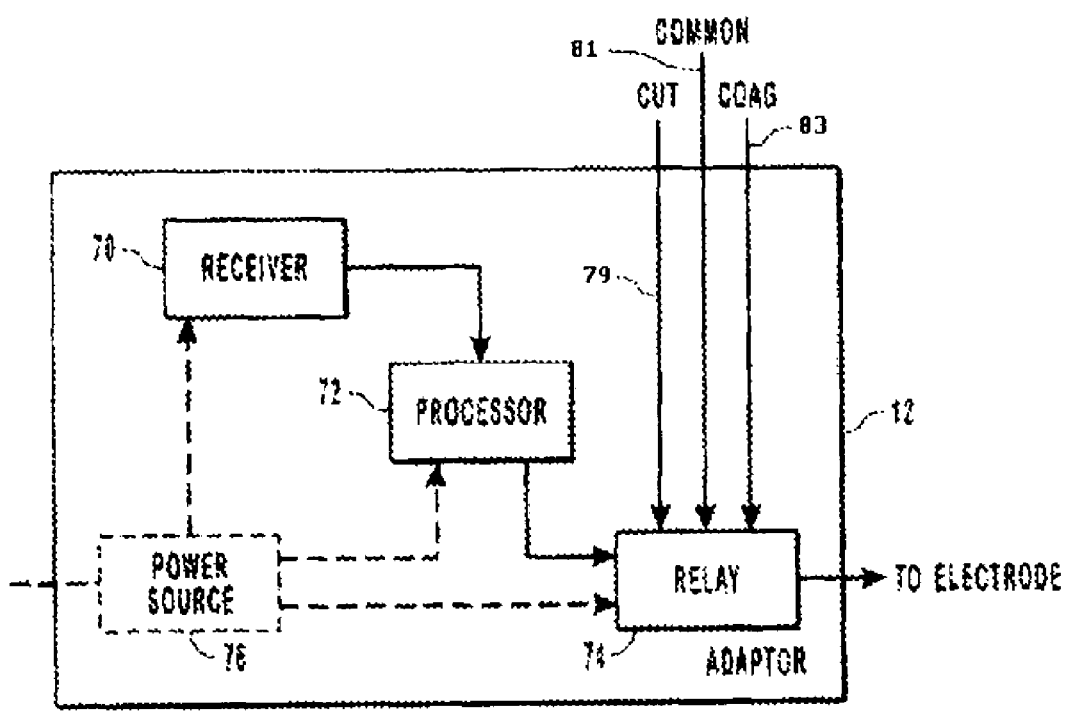

The electrosurgical generator 210 is in electrical communication with electrosurgical instrument 220 by way of conductor 214. The electrosurgical instrument 220 may have a similar configuration to electrosurgical instrument 20 (FIG. 2) described previously. In addition, electrosurgical instrument 220 is adapted to receive the electrosurgical energy along conductor 214 rather than through contacts 48 (FIG. 2). For instance, and as shown in FIG. 9, conductor 214 extends into an interior 222 of electrosurgical instrument 220 to connect to one or more conductive members 90. Upon activating input device 54, electrosurgical energy is delivered to conductive members 90 and subsequently to an electrode or tip, such as electrode or tip 30 shown in FIG. 3. Optionally, conductor 214 connects to input device 54 to allow input device 54 to prevent delivery of electrosurgical energy to conductive members 90 until input device 54 is activated. Because electrosurgical generator 210 only delivers the RF signals or electrosurgical energy upon receiving a signal indicating that input device 54 is activated, this functionally acts as a safety feature for system 200 (FIG. 8).

As may be understood from the above, the various embodiments described herein are adapted to deliver wireless signals to an electrosurgical generator along a wireless control signal path. This control signal path utilizes electromagnetic radiation, thereby eliminating the need for direct physical connection between the electrosurgical generator and the electrosurgical instrument. Rather, control signals are transmitted from the electrosurgical instrument to the electrosurgical generator and/or an associated adapter to initiate deliver of electrosurgical energy to the electrosurgical instrument. In this manner, even when a conductor extends between the electrosurgical instrument and the electrosurgical generator, the electrosurgical system may initiate delivery of electrosurgical energy without the need for a physical control path between the electrosurgical generator and the electrosurgical instrument. Consequently, the methods, systems, and instruments alleviate the problems associated with corded electrosurgical instruments and allow a physician to perform electrosurgical procedures in a less strenuous manner within a safer environment than is currently the case.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. An electrosurgical instrument adapted for use with an electrosurgical generator, the electrosurgical instrument comprising:
    a hand piece adapted to receive electrosurgical energy from the electrosurgical generator, wherein at least a portion of the electrosurgical energy passes through a physician using the hand piece as the electrosurgical energy is delivered from the electrosurgical generator to the hand piece, the hand piece comprising a recess adapted to receive an electrode adapted to discharge the electrosurgical energy; and a transmitter coupled to the hand piece, the transmitter being adapted to transmit a wireless signal that initiates delivery of the electrosurgical energy from the electrosurgical generator, through the physician, and to the hand piece.

2. The electrosurgical instrument as recited in claim 1, further comprising at least one contact coupled to the hand piece, the at least one contact being adapted to receive electrosurgical energy.

3. The electrosurgical instrument as recited in claim 2, wherein the at least one contact is positioned upon the hand piece at a location selected from the group consisting of a top of the hand piece, a bottom of the hand piece, a side of the hand piece, a proximal end of the hand piece, and a distal end of the hand piece.

4. The electrosurgical instrument as recited in claim 2, wherein the at least one contact forms the hand piece.

5. The electrosurgical instrument as recited in claim 2, wherein the at least one contact forms a portion of the hand piece.

6. The electrosurgical instrument as recited in claim 1, further comprising at least one contact electrically communicating with the electrosurgical generator and the electrode and being adapted to contact the physician to allow the at least a portion of the electrosurgical energy to pass through the physician.

7. The electrosurgical instrument as recited in claim 6, wherein at least one of the one or more contacts is adapted to cooperate with a conductive glove worn by the physician.

8. The electrosurgical instrument as recited in claim 1, further comprising an input device coupled to the hand piece, the input device being adapted to initiate delivery of the wireless signal to the electrosurgical generator.

9. The electrosurgical instrument as recited in claim 1, wherein the wireless signal comprises a signal having a wavelength selected from the group consisting of radio, microwave, or infrared.

10. The electrosurgical instrument as recited in claim 1, wherein at least one of the hand piece and the one or more contacts is at least one of washable, sterilizable, cleanable, and reusable.

11. An electrosurgical instrument adapted to receive electrosurgical energy from an electrosurgical generator, the electrosurgical instrument comprising:
a hand piece comprising a proximal end and a distal end, the distal end being adapted to receive an electrosurgical electrode; and
one or more electrical contacts coupled to the hand piece, the one or more contacts being contactable by a physician to enable electrosurgical energy to pass from the electrosurgical generator to the electrosurgical electrode through the physician.

12. An electrosurgical instrument as recited in claim 11, wherein the electrosurgical energy is delivered to the hand piece in response to activation of at least one input device.

13. An electrosurgical instrument as recited in claim 12, wherein the input device is manipulatable by the physician.

14. An electrosurgical instrument as recited in claim 12, wherein the input device is coupled to the hand piece and is adapted to initiate delivery of the electrosurgical energy.

15. An electrosurgical instrument as recited in claim 12, wherein the input device is remote from the hand piece and is adapted to initiate delivery of the electrosurgical energy.

16. An electrosurgical instrument as recited in claim 12, further comprising a transmitter coupled to the hand piece, the transmitter being adapted to transmit a wireless signal that initiates delivery of the electrosurgical energy.

17. An electrosurgical system for use by a physician in performing an electrosurgical procedure, the system comprising:
an electrosurgical generator adapted to generate current;
an electrosurgical instrument adapted to receive the current from the electrosurgical generator, the electrosurgical instrument comprising:
a hand piece adapted to be held by the physician, a first end of the hand piece being adapted to receive an electrosurgical electrode; and
a transmitter coupled to the hand piece, the transmitter being adapted to transmit a wireless signal that initiates delivery of the current from the electrosurgical generator to the hand piece; and
an electrode disposed electrically between the electrosurgical generator and the physician such that current from electrosurgical generator is transmitted from the electrode to the hand piece at least partially through the physician.

18. The electrosurgical system as recited in claim 17, wherein the electrosurgical instrument further comprises at least one contact coupled to the hand piece, the at least one contact being adapted to receive the current upon the physician touching the at least one contact and the electrode.

19. The electrosurgical system as recited in claim 17, wherein the electrode comprises a sheet of material having an effective bulk impedance equal to or greater than about 4,000 Ω·cm.

20. The electrosurgical system as recited in claim 17, wherein the electrosurgical system further comprises at least one input device, the at least one input device being adapted to initiate delivery of the wireless signal to the electrosurgical generator.

* * * * *

UNITED STATES PATENT AND TRADEMARK OFFICE
CERTIFICATE OF CORRECTION

| | | |
|---|---|---|
| PATENT NO. | : 8,932,280 B2 | Page 1 of 2 |
| APPLICATION NO. | : 12/957177 | |
| DATED | : January 13, 2015 | |
| INVENTOR(S) | : Isaacson et al. | |

It is certified that error appears in the above-identified patent and that said Letters Patent is hereby corrected as shown below:

Drawings
Sheet 3, replace Figure 3 with the figure depicted on the attached page, wherein reference number "82" is replaced with "81", reference number "84" is replaced with "83", and reference number "80" is replaced with "79"

Specification

Column 2
Line 35, change "loose" to -- lose --

Column 3
Line 10, change "the)" to -- the --

Column 7
Line 48, change "configuration" to -- configurations --
Line 36, change "electrosurgical is" to -- electrosurgical energy is --

Column 11
Line 39, change "degrees)" to -- degrees --

Column 12
Line 28, change "10 (FIG. 2)" to -- 10 (FIG. 1) --
Line 32, change "10 (FIG. 2)" to -- 10 (FIG. 1) --
Line 60, change "input Input" to -- input --

Column 13
Line 53, change "complete" to -- completely --

Signed and Sealed this
Ninth Day of February, 2016

Michelle K. Lee
*Director of the United States Patent and Trademark Office*